(12) United States Patent
Heide et al.

(10) Patent No.: US 9,567,992 B2
(45) Date of Patent: Feb. 14, 2017

(54) METHODS AND DEVICES FOR MODULATION OF THE OPERATING POINT OF LIQUID PUMPS IN MEDICAL TREATMENT DEVICES

(71) Applicant: Fresenius Medical Care Deutschland GmbH, Bad Homburg (DE)

(72) Inventors: Alexander Heide, Eppstein (DE); Pascal Kopperschmidt, Dittelbrunn (DE); Ulrich Moissl, Karben (DE); Wolfgang Wehmeyer, Tuebingen (DE); Christoph Wiktor, Gelnhausen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 471 days.

(21) Appl. No.: 13/863,527

(22) Filed: Apr. 16, 2013

(65) Prior Publication Data
US 2013/0280104 A1 Oct. 24, 2013

Related U.S. Application Data

(60) Provisional application No. 61/624,542, filed on Apr. 16, 2012.

(30) Foreign Application Priority Data

Apr. 16, 2012 (DE) ......................... 10 2012 007 412

(51) Int. Cl.
*F04B 43/00* (2006.01)
*F04B 43/12* (2006.01)
(Continued)

(52) U.S. Cl.
CPC ............ *F04B 43/12* (2013.01); *A61M 1/101* (2013.01); *A61M 1/1039* (2014.02);
(Continued)

(58) Field of Classification Search
CPC .. A61M 1/1086; A61M 1/1039; A61M 1/101; F04B 43/1253; F04B 11/0058; F04B 43/0081; F04B 43/12; F04D 15/0066
See application file for complete search history.

(56) References Cited

U.S. PATENT DOCUMENTS 4,229,299 A   10/1980   Savitz et al.
4,795,314 A   1/1989   Prybella et al.
(Continued)

FOREIGN PATENT DOCUMENTS

DE   2651962   5/1978
DE   3326785   2/1985
(Continued)

*Primary Examiner* — Charles Freay
*Assistant Examiner* — Thomas Cash
(74) *Attorney, Agent, or Firm* — Jacobson Holman, PLLC.

(57) ABSTRACT

Fluid pumps and medical treatment devices, in particular dialysis machines, include devices configured such that operating pressures and flow rates of the fluid pumps assume desired characteristics, in particular constant values or controlled profiles. The operating point of a peristaltic hose roller pump is adjusted based on an angle of rotation of a pump rotor, or by adjusting the operating point of a centrifugal pump in accordance with a profile.

14 Claims, 5 Drawing Sheets

(51) Int. Cl.
*F04B 15/00* (2006.01)
*A61M 1/10* (2006.01)
*F04B 11/00* (2006.01)
*F04D 15/00* (2006.01)

(52) U.S. Cl.
CPC ........ *A61M 1/1086* (2013.01); *F04B 11/0058* (2013.01); *F04B 43/0081* (2013.01); *F04B 43/1253* (2013.01); *F04D 15/0066* (2013.01)

(56) References Cited

U.S. PATENT DOCUMENTS

| | | | |
|---|---|---|---|
| 6,046,046 A * | 4/2000 | Hassanein | A01N 1/0247 435/284.1 |
| 7,914,478 B2 * | 3/2011 | Kumazaki | A61M 25/1011 604/6.11 |
| 9,005,153 B2 | 4/2015 | Kopperschmidt et al. | |
| 2003/0150809 A1 * | 8/2003 | Bomberger | A61M 1/34 210/651 |
| 2005/0019167 A1 | 1/2005 | Nusser et al. | |
| 2009/0099498 A1 * | 4/2009 | Demers | A61M 1/106 604/6.09 |
| 2011/0201990 A1 * | 8/2011 | Franano | A61M 1/367 604/9 |
| 2013/0338559 A1 * | 12/2013 | Franano | A61M 1/101 604/4.01 |

FOREIGN PATENT DOCUMENTS

| | | |
|---|---|---|
| DE | 3726452 | 2/1989 |
| DE | 3922686 | 1/1991 |
| DE | 19611637 | 10/1997 |
| EP | 0004600 | 10/1979 |
| EP | 2 386 324 | 11/2011 |
| EP | 2386324 | 11/2011 |
| WO | WO 02088547 | 11/2002 |
| WO | WO 2010/020380 | 2/2010 |

* cited by examiner

METHODS AND DEVICES FOR MODULATION OF THE OPERATING POINT OF LIQUID PUMPS IN MEDICAL TREATMENT DEVICES

BACKGROUND OF THE INVENTION

1. Field of invention

The invention relates to the field of liquid pumps in medical treatment devices.

2. Description of the Prior Art

Medical treatment devices are in particular blood treatment devices. Blood treatment devices comprise dialysis machines which can be subdivided into hemodialysis machines and machines for performing automated peritoneal dialyses.

Dialysis is a method of purifying the blood of patients with acute or chronic renal insufficiency. Fundamentally, a distinction is made here between methods having an extracorporeal blood circulation such as hemodialysis, hemofiltration or hemodiafiltration (summarized below under the term "hemodialysis") and peritoneal dialysis, which does not have an extracorporeal blood circulation.

In hemodialysis the blood in an extracorporeal circulation is passed through the blood chamber of a dialyzer, which is separated from a dialysis fluid chamber by a semipermeable membrane. The dialysis fluid chamber has a dialysis fluid containing the blood electrolytes in a certain concentration flowing through it. The substance concentration of the dialysis fluid corresponds to the concentration of the blood of a healthy person. During the treatment, the patient's blood and the dialysis fluid are passed by both sides of the membrane, usually in countercurrent at a predetermined flow rate. Substances that must be eliminated in urine diffuse through the membrane from the blood chamber into the chamber for the dialysis fluid, while at the same time electrolytes present in the blood and in the dialysis fluid are diffusing from the chamber of the higher concentration to the chamber of the lower concentration. If a pressure gradient is built up from the blood side to the dialysate side on the dialysis membrane, for example, due to a pump which withdraws dialysate from the dialysate circulation downstream from the dialysis filter on the dialysate side, water enters the dialysate circulation from the patient's blood through the dialysis membrane. This ultrafiltration process leads to the desired withdrawal of water from the patient's blood.

In hemofiltration, ultrafiltrate is withdrawn from the patient's blood by applying a transmembrane pressure in the dialyzer without passing dialysis fluid by the membrane of the dialyzer on the side opposite the patient's blood. In addition, a sterile and pyrogen-free substitute solution may be added to the patient's blood. We speak of pre-dilution or post-dilution, depending on whether this substitute solution is added upstream or downstream from the dialyzer. The mass exchange takes place by convection in hemofiltration.

Hemodiafiltration combines the methods of hemodialysis and hemofiltration. Thus a diffusive mass exchange takes place between the patient's blood and the dialysis fluid through the semipermeable membrane of the dialyzer, and the plasma water is also filtered through a pressure gradient on the membrane of the dialyzer.

Plasmapheresis is a method blood plasma is separated from corpuscular components of blood (cells). The separated blood plasma is purified or replaced by a substitution solution and return to the patient.

In peritoneal dialysis, the patient's abdominal cavity is filled with a dialysis fluid through the abdominal wall such that the dialysis fluid has a concentration gradient with respect to the endogenous fluids. The toxic substances present in the body enter the abdominal cavity through the peritoneum, which acts as a membrane. After a few hours the dialysis fluid, now spent, which is in the patient's abdominal cavity is replaced. Water can travel from the patient's blood through the peritoneum and into the dialysis fluid by osmotic processes, thereby withdrawing water from the patient.

Dialysis methods are usually performed with the help of automatic dialysis machines such as those already distributed by the applicant under the brand name 5008 or sleep.safe.

To convey fluids in medical treatment devices, pumps of different designs are used. Peristaltic hose roller pumps are often used with machines having an extracorporeal blood circulation, such as hemodialysis machines. These hose roller pumps are often used in medical technology because they permit contactless transport of a fluid. In addition, they theoretically supply a flow which is proportional to the rotational speed over a wide range independently of the flow resistances upstream and downstream from the pump. In the case of a blood pump in extracorporeal treatment methods, the incoming (suction) side is referred to as the arterial side with an adjusted vacuum of typically approx. −100 to −300 mm mercury column in comparison with the outside pressure, and the efferent side is referred to as the venous side with a reduced pressure in comparison with the outside pressure.

DE3326785A1 discloses a typical embodiment of such an occlusive hose roller pump, according to which the delivery medium is moved by means of a periodically occluded hose.

In terms of the basic concept, a roller pump has a stator and a rotor. The stator is designed on the pump housing and has a recess with whose smoothly running vertical wall a pump hose is in contact. The area in which the pump hose is in contact with the wall forms the pump bed, which has the contour of a detail of a circle.

The axis of rotation of a rotor having rotatably mounted rollers on its free ends passes through the midpoint of this section of a circle. In rotation of the rotor in the working direction, the rollers come in contact with the pump hose, which is in contact with the circular contour of the circle of the pump bed and compress it to such an extent as it rotates further that it forms a fluid-tight seal (occlusive).

The delivery medium in the pump hose is conveyed further by further rolling of the rollers on the pump hose. In most cases, such a rotary pump has two rollers, which are mounted on the rotor in such a way that the connecting line passes through the axis of rotation of the rotor.

Other types of pumps which may be used include, for example, centrifugal pumps, diaphragm pumps or gear pumps.

The type of pump is definitive for the stress on the medium to be conveyed. This is important in particular in the case of an extracorporeal blood circulation because the blood can be damaged by pumping, and this may destroy erythrocytes, i.e., the red blood cells in particular (hemolysis). This may occur mechanically in particular, e.g., due to squeezing inside a blood hose or due to excessively high pressures.

A pulsatile non-steady-state flow, which is caused by the continuing engagement of the rollers in the pump hose segment, is characteristic of a hose roller pump. When the rollers mesh with the hose segment, the hose is squeezed together, thereby displacing the fluid. This fluid is displaced both in the direction of flow and opposite the direction of flow. Upstream from the roller, the displaced fluid is superimposed on the flow in the direction of the pump during ongoing operation and thus results in a short-term net reduction inflow, so that the arterial pressure becomes less negative until the hose is completely occluded. Then the fluid in the hose is accelerated again and the arterial pressure drops again. Downstream from the hose roller pump there is a sudden drop in pressure as soon as the roller emerges from the pump segment and a pressure equalization occurs between the reduced pressure in the segment between the rollers, this segment having been enclosed so far, and the excess pressure downstream from the pump.

Pressure peaks (and/or flow peaks) may occur in the area of the puncture site of the needle which returns the extracorporeal blood to a patient, and may cause shearing forces which in the extreme case may lead to thrombosis (coagulation) on the vascular walls and may even lead to hemolysis. Upstream from the pump, high shearing forces may also occur in equalization between high- and low-pressure systems.

In addition, hose roller pumps may also be used in the area of hemodialysis for the addition of blood-thinning substitute fluids. The pressure pulses generated in this way influence the blood to be thinned although to a lesser extent than with the blood pump at least at the location where the substitute and the blood are mixed.

Another type of pump that is used is the impeller pump or centrifugal pump. Centrifugal pumps essentially contain a housing to hold an impeller to which a magnet is fixedly connected. The magnet can be rotated by a second rotating magnet contained in a stationary base so that the impeller is made to rotate and the liquid in the housing is moved from a liquid inlet to a liquid outlet. Due to the operating principle, centrifugal pumps supply a constant volume flow so that the output pressure of the fluid pumped is a function of the input pressure, the viscosity of the fluid and the rotational speed. Pressure pulses in the fluid conveyed as in the case of peristaltic pumps do not occur with centrifugal pumps in normal operation at a constant rate of rotation of the impeller. Therefore, this prevents hemolysis caused by pulsatile conveyance of blood.

When used in the extracorporeal blood circulation, in particular in hemodialysis treatments, it is often necessary to add medication to blood in a controlled manner. A typical example of medication is the addition of anticoagulants such as heparin in hemodialysis treatments to prevent the blood from coagulating in the extracorporeal blood circulation and thereby prevent the fine hollow fibers of the dialysis filter from becoming clogged.

Syringe pumps, which add heparin or another anticoagulant (e.g., citrate) to the blood upstream from a dialysis filter, are often used for this purpose. However, it is also provided that a medication may also be added to the blood by delivering the medication through a special device and into drip chamber.

EP2386324A1 discloses such a device. A medication dosing apparatus which releases doses of a medication into the drip chamber on the basis of pressure pulses in the drip chamber is proposed there. The pressure pulses are generated here by the pulsatile non-steady-state operation of a peristaltic pump which delivers a fluid, preferably blood, into the drip chamber. Thus a pulsating air pressure characteristic develops via the fluid level inside the drip chamber in the cycle of the peristaltic pump, leading to regular dispensing of droplets of medication into the drip chamber.

So far, when using steadily delivering peristaltic pumps, it has not been possible to control the dosing of medication in a variable manner, i.e., to suspend it or have it occasionally occur more often. With centrifugal pumps it has not been possible at all so far to operate the medication dosing apparatus proposed in EP2386324A1 because of the lack of pressure fluctuations.

SUMMARY OF THE INVENTION

The object of the present invention is therefore to create devices and methods which control a pump, so that the occurrence of pressure peaks and/or flow peaks in the delivery medium of the pump is avoided or that they follow a predetermined profile.

This object is achieved by the device and the method described herein. Preferred embodiments of the invention are are also described herein.

It is thus provided that the operating point of a peristaltic pump is to be altered as a function of the angle formed by the rotor with any stationary point. In addition, it is provided that the operating point of a centrifugal pump which drives a medication dosing device is to be altered in accordance with a profile which includes at least one change from a first operating point to a second operating point and a change from the second operating point to the first or a third operating point such that the second operating point comprises at least one operating parameter which is greater or less than this operating parameter of the first and third operating points.

The operating point of a peristaltic pump or a centrifugal pump is understood to refer to at least one of the operating parameters of the pump. Operating parameters include in particular the input and output pressure in the pumped fluid, delivery rates of the pumped fluid at the inlet and outlet of the pump, the angular velocity of the rotor of the peristaltic pump, the angle formed by the rotor of the peristaltic pump with any stationary point, the rotational speed of the impeller of the centrifugal pump and the power supply voltage, power supply current and the power consumption of the electric motor driving the pump.

It is important that the list of operating parameters enumerated cannot be influenced independently of one another. By varying the operating point by varying at least one operating parameter, numerous other operating parameters are also changed automatically. Thus an increase in the rotational speed of a centrifugal pump usually also results in a higher flow rate at the inlet and outlet of the pump, and also causes a higher differential pressure between the inlet and the outlet in the fluid being conveyed. Likewise the power consumption by the pump is also increased.

Embodiments in which certain operating parameters are altered are described below for the peristaltic pump and the centrifugal pump. It is clear to those skilled in the art that the invention can readily be applied to embodiments in which other operating parameters are altered. What is important is the consequences of altering the operating point of the pump by changing one operating parameter or the other.

An embodiment in which the angular velocity of the rotor of the peristaltic pump is modulated periodically to reduce the peaks in the fluid pressure caused by the rollers moving into and out of the pump bed or to completely suppress these peaks in the ideal case is suitable for the device with the peristaltic pump. Due to the design, the pump bed in which the hose is inserted forms approximately a semicircle so that the interaction of the hose rollers with the hose occurs during one half of a revolution.

The angular velocity of the rotor of the peristaltic pump is ideally modulated so that there is a constant fluid pressure. However, if a pressure pulse in the fluid is desired to achieve a controlled delivery of the medication in a device consisting of a drip chamber and a dosing device arranged downstream, as described in EP 2 386 324 A1, then a second modulation of the angular velocity may be superimposed on the first modulation to achieve a controlled pressure pulse in the fluid.

The angular velocity of the rotor of the peristaltic pump is altered as a function of the current position of the rotor in one embodiment, i.e., as a function of the angle formed by the rotor with any stationary point.

In contrast with peristaltic pumps, centrifugal pumps do not produce any pressure pulses in the fluid delivered during operation. Centrifugal pumps are approximately constant pressure sources whose output pressure corresponds to the input pressure plus the pressure generated by the pump. This pressure generated by the pump depends on the viscosity of the fluid being pumped and the rotational speed of the impeller of the centrifugal pump.

If it is desirable to create controlled pressure pulses in an application consisting for example, of a centrifugal pump with a device which is operated downstream and consists of a drip chamber and a dosing device as described in EP2386324A1, then the operating point of the impeller can be modulated accordingly to generate such pressure pulses.

The operating point here changes essentially in a pulse form. In other words, the operating point, which characterized at least by an operating parameter, for example, due to the rotational speed of the impeller, becomes greater at first and then becomes smaller again after a comparatively short time. An alternative embodiment provides that the operating point at first becomes smaller and then becomes greater again. If a peristaltic pump is used instead of a centrifugal pump, then the operating point is characterized by the angle formed by the rotor with any stationary point, for example.

Depending on the pump embodiment and the installed or connected hose, the input pressure and output pressure and/or the pump rates respond differently to changes in operating points. The pump itself and the hose inserted into it or connected to it are thus subject to variances due to production.

In this way, for example, the angles of the rotor of a hose roller pump at which the hose rollers engage in the hose and are lifted up from it again are varied.

In addition, the thickness of the hose and with that the flexibility of the hose also varies from one type of hose to the next but also within the same type of hose due to manufacturing-induced variances.

The flexibility of the hose is important for the restoring force of the hose among other things. The restoring force of the hose is in turn important for the period of time required by hose to restore its original shape after it has been compressed for example, by a hose roller pump. Thus the course of the fluid pressure over time within the hose also depends on the varying restoring force of the hose among other things.

Therefore, a calibration process may be provided for each specific pump and inserted or connected hose. In such a calibration process, a control unit varies the operating point of the pump according to a calibration profile and picks up at least one operating parameter such as the fluid pressure or the pump rate at the inlet or outlet of the pump and assigns the at least one operating parameter to the respective current operating point.

For example, the angular velocity (depending on the rotor angle) or the rotational speed of the rotor and/or the pump may be varied in a targeted manner and the respective angular velocity (depending on the rotor angle) and/or the rotational speed may be assigned to a fluid pressure at the inlet and/or outlet of the pump.

Thus any combination of pump and inserted or connected hose can be measured in a calibration phase to obtain an unambiguous relationship between the operating point and/or the change in the operating point and the parameters that depend on this operating point and/or the change in the operating point and/or the change therein such as the fluid pressure upstream or downstream from the pump or the pump rate.

The relationship thereby obtained can be stored in the form of a table, for example, in a memory. By means of a mathematical operation, a function which maps the table can also be formed from this table. This function may be used in a control circuit to determine the necessary operating point for the respective desired parameter such as the fluid pressure at the pump outlet.

Another embodiment of the invention relates to a system of at least two pumps which convey fluid in the same fluid cycle. Such systems of multiple pumps conveying fluid in the same fluid circulation are known from dialysis. Thus a pump for delivering blood replacement fluid (substitute) is often arranged downstream from a peristaltic blood pump in a hemodialysis machine. This pump may be embodied as a syringe pump, in which the plunger of the syringe can be moved forward and in reverse by a controllable drive (electric, pneumatic or hydraulic).

Other embodiments of substitute pumps comprise for example, gear pumps, diaphragm pumps, hose roller pumps or centrifugal pumps.

The substitute pump can deliver the substitute for example, directly into a venous drip chamber to which a medication dosing device may be connected. Such a system of blood pump and substitute pump delivers a different fluid to each fluid circulation.

However, systems of pumps arranged in succession are also conceivable in which pumps of the same or different types are used and deliver the same fluid. It is thus conceivable that a second pump embodied as a centrifugal pump, for example, is arranged downstream from a peristaltic blood pump.

Regardless of how the pumps are arranged with respect to one another, it is essential for the invention that the operating point of each pump acts on the fluid pressure and/or the delivery rate at least at one single point of a fluid circulation.

For example, it is possible to achieve the effect that the fluid pressure and/or the delivery rate is adjustable by modulation of the operating point of at least one pump at least at this one point.

For example, through appropriate control of the piston of the substitute pump, the pressure in the venous drip chamber may be adjusted to any characteristic regardless of whether or not the blood pump, which is also delivering fluid into the venous drip chamber.

For example, a rise in pressure generated by a blood pump upstream can be counteracted by synchronized retraction of the piston of a substitute pump, which is embodied as a syringe pump, which delivers fluid into the same fluid circulation downstream from the blood pump.

It is also conceivable that, with pumps of the same or different type, which are arranged one after the other fluidically, delivering the same fluid, the operating points of each pump are modulated individually. Thus, for example, with a system consisting of a hose roller pump and a centrifugal pump downstream, the hose roller pump may be modulated in such a way that pressure fluctuations at its pump outlet are minimized and the operating point of the downstream centrifugal pump is modulated, so that pressure pulses for controlling a medication dosing device in the manner described above are generated at the pump outlet thereof.

Combinations of any conceivable type of pump with at least two pumps are conceivable wherein the operating points of each pump used can be modulated like a profile.

The embodiments of the invention are explained further in the detailed description of the figures.

BRIEF DESCRIPTION OF THE DRAWINGS

The following figures are presented to facilitate an understanding of the invention and they show exemplary embodiments of the present invention.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
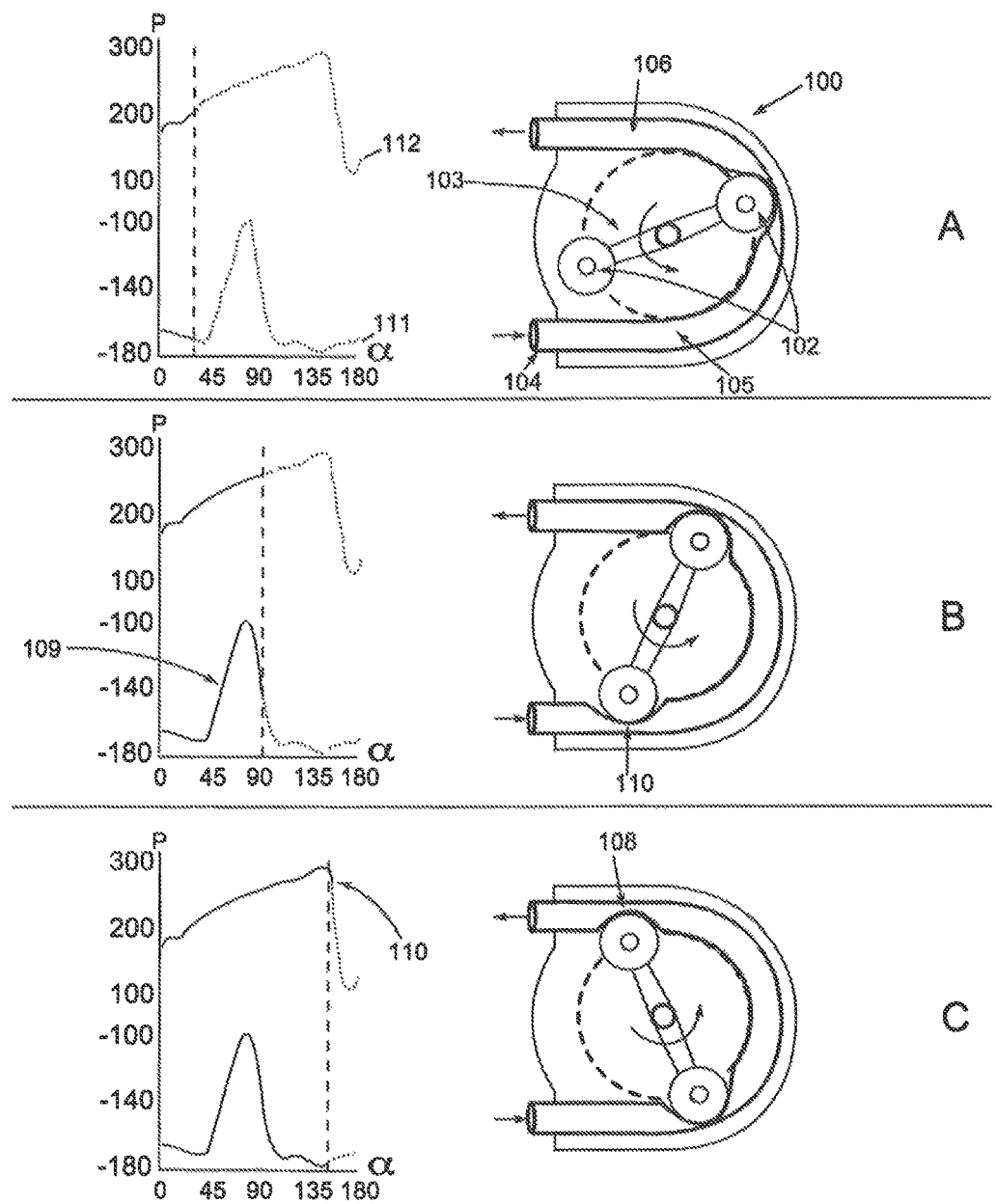
FIG. 1 shows on the basis of three phases the pumping operation when using a traditional peristaltic hose roller pump.

FIG. 1 is subdivided into three phases A, B and C, each having a peristaltic hose roller pump 100 with an inserted hose 104. The peristaltic pump comprises a rotor 103 with rotatably mounted rollers 102 which engage in the elastic hose 104 and deliver the fluid within the hose 104 due to the rotation of the rotor (counterclockwise in FIG. 1).

Phases A, B and C in FIG. 1 differ in the position of the rotor. Each diagram shows the output pressure 112 at the left, next to the hose roller pump, and the input pressure 111 prevailing inside the hose 104 downstream and upstream, respectively, plotted as a function of the adjustment angle α of the rotor.

The broken vertical line characterizes here the current position angle of the rotor 103. Past pressure curves are shown at the left of this line and future curves are shown as interrupted lines at the right of this line.

Since the pumping operation takes place within one half of a rotation of the rotor due to the geometry of the hose roller pump, the labeling of the abscissa ends at 180 (degrees). The ordinate shows the fluid pressure in mm mercury column with respect to the outside pressure. After half a rotation, the pump operation begins again, and then the previously leading hose roller, i.e., the hose roller closer to the pump outlet in the direction of flow, is then the currently trailing hose roller and vice versa.

The pressure characteristics upstream and downstream from the pump are essential for an understanding of the invention. In phase A the right roller 102 occludes the hose completely and pushes the fluid which is in the hose section 106 counterclockwise toward the pump outlet. The fluid in the hose section 105 is also delivered in the direction of the pump outlet due to the hose moving back into its original shape.

The fluid pressure increases linearly in the hose section 106 whereas the fluid pressure decreases linearly in the hose section 105.

In phase B, the trailing lower hose roller pump engages with the pump bed for the first time and squeezes the hose at the location 110. There is thus a displacement of volume there, reflected in the sudden jump in pressure 109 in the hose section 105. The hose section 106 is not affected by this volume displacement because the leading hose roller completely occludes the hose.

In phase C, the leading roller is lifted up from the pump bed and releases the hose 104 at the location 108. Then there is an equalization of pressure between the hose sections 105 and 106. This is reflected in the drop in pressure 110.

This procedure is repeated with each half revolution so there is a periodic pulsatile fluid transport with the pressure pulses shown in FIG. 1. The pressure and fluid flow are proportional to one another, so that the fluid flow is higher, the higher the pressure and the lower the flow resistance.

One object of the invention is to reduce these pressure pulses or ideally suppress them completely.

Figure 2:
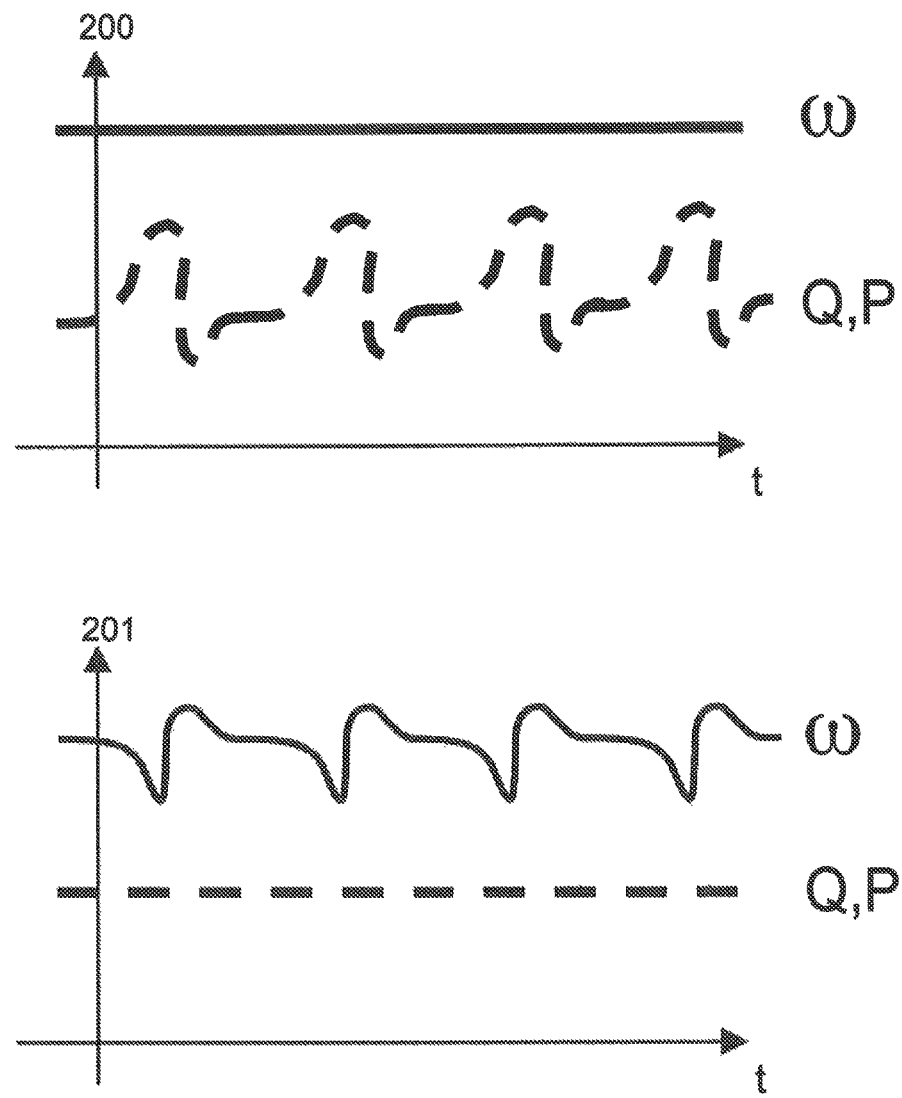
FIG. 2 shows on the basis of two diagrams as an example the change in the operating point of a hose roller pump due to modulation of the angular velocity of the hose roller pump.

FIG. 2 illustrates on the basis of two diagrams the modulation of the angular velocity of the rotor of a hose roller pump according to the invention, as shown in FIG. 1 to generate a constant fluid pressure and a constant fluid flow.

The diagram 200 shows the curve of the fluid pressure P at the pump outlet and/or the fluid flow Q at a constant angular velocity ω. This shows the typical pulsatile curve of pressure and flow as in the diagrams in FIG. 1.

In contrast with that the diagram 201 shows the fluid pressure P at the pump inlet or outlet and/or the fluid flow Q when the angular velocity is modulated according to the invention. In principle, the change in the angular velocity in the diagram 201 follows a profile which is in inverse ratio to the change in the fluid pressure P and/or the fluid flow Q in diagram 200. In other words, if the pressure and/or flow in diagram 200 increase, then the angular velocity in diagram 201 decreases accordingly and vice versa.

Thus the angular velocity according to the invention depends on the angle of rotation of the rotor of the hose roller pump. The angle of the rotor can be made known by any sensors of the control unit which prompt a corresponding angular velocity of the rotor on the basis of the angle, which is then known. Exemplary embodiments of the sensors for detecting the angle of rotation of the rotor include potentiometers whose resistance depends on the angle of rotation or Hall sensors which deliver signals corresponding to the angle of rotation.

However, it is also conceivable that the hose roller pump is driven by a stepping motor, which rotates defined angles with a corresponding electrical control. The angle of rotation can thus be learned by a control unit at any time. Only one starting point of the angle of rotation need be made known to the control unit.

In addition to keeping the fluid pressure or the fluid flow constant, these variables may be regulated at any predetermined profile according to the invention in that a second modulation of the angular velocity of the rotor is superimposed on the first modulation which leads to a constant fluid pressure and/or flow. This may be desired, for example, when a medication dosing device which is driven by the peristaltic pump is present downstream from the pump.

According to another embodiment of the invention, as an alternative to the angle of rotation or in addition to the angle of rotation, additional variables are measured and sent to the control unit. These additional variables may be the fluid pressure and/or the fluid flow at the pump inlet and/or at the pump outlet. It is also conceivable to return of the electrical pump current, i.e., the current which is supplied to the drive motor of the pump. The control unit here regulates the angular velocity of the rotor of the hose roller pump based on the additional variables, so that the pressure and/or the flow assume desired values.

Figure 3:
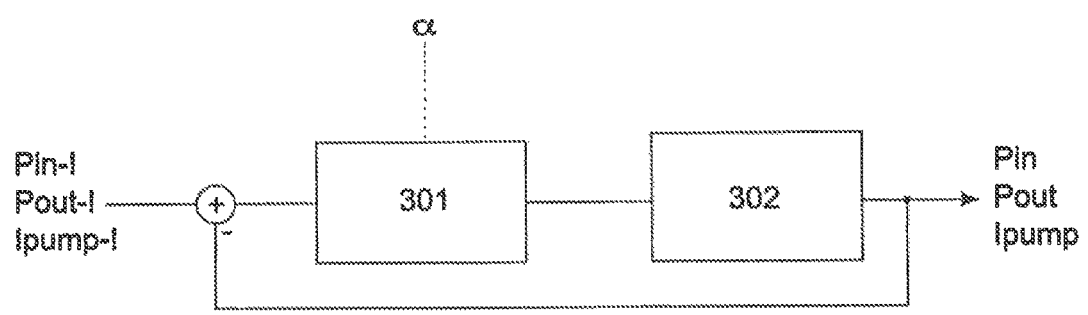
FIG. 3 shows a regulating system according to the invention for determining a certain angular velocity of the rotor of a hose roller pump.

FIG. 3 shows a corresponding control circuit in which the input pressure and the output pressure are compared with corresponding setpoint values and a certain angular velocity is determined from them.

One possible additional or exclusive variable which can be supplied to the control circuit according to FIG. 3 is the engine current of the hose roller pump. It has been found that the engine current and in particular the output pressure of the hose roller pump are proportional to one another.

The control circuits shown in FIG. 3 receive at least one of the additional variables, namely the input pressure Pin, the output pressure Pout and the electrical pump current Ipump with the setpoint values Pin-!, Pout-! and Ipump-! and the control deviation is sent to a control unit 301. The control unit 301 thus receives at least one operating parameter of the pump. This control unit calculates on the basis of the control deviation a corresponding prevailing angular velocity and sends a corresponding signal to the pump 302, which causes the pump to rotate at the calculated angular velocity. Optionally and as shown with a dotted line in FIG. 3, the angle of rotation a of the pump rotor is additionally sent to the control unit 301. The additional variables here are measured by suitable sensors, for example, pressure sensors, flow rate sensors, electrical sensors (current measurement, voltage measurement).

The control unit 301 can access the data determined in a calibration phase when determining an operating point for the pump. From these calibration data which are representative of the behavior of the pump parameters as a function of the operating point, the control unit then calculates the respective current operating point which leads to maintaining the setpoint values. To do so, the control unit may access a stored table having different operating points and pump parameters assigned to them, for example, an output pressure for a certain angular velocity and a certain rotor angle or an output pressure for a certain rotational speed. Alternatively, however, this assignment may also be made on the basis of a mathematical function which obtained from the data from the calibration phase.

If the feedback of the additional variables replaces the feedback of the angle of rotation of the rotor, then this advantageously eliminates the need for the corresponding sensors for the angle of rotation.

If the feedback of the additional variables supplements the feedback of the angle of rotation of the rotor, then potentially dangerous situations can be inferred from knowledge both the fluid pressure (or flow) and the angle of rotation.

One such potentially dangerous situation is, for example, occlusion of the hose downstream from the hose roller pump. Such an occlusion may occur, for example, when a filter, for example, a dialysis filter becomes clogged downstream from the pump. Due to the design the hose roller pump occludes the hose in normal operation. If the flow resistance increases due to occlusion, the pressure at the pump outlet increases greatly and may cause the hose to rupture or may cause rupturing of hollow fibers in the dialysis filter through which the patient's blood is flowing. In both cases, there is blood loss by the patient.

To prevent this, hose roller pumps are often equipped with rollers in spring mounts in the direction of the access of rotation of the roller. The rollers here are pressed against the hose by springs with a certain spring force (occlusive force). If the fluid pressure in the hose exceeds this spring force, then the rollers move in the direction of the axis of rotation of the rotor. As a result of this they no longer completely occlude the inserted hose, and there is a pressure limitation in the fluid delivered.

The embodiment with fluid pressure or fluid flow feedback at the pump outlet according to the invention, for example, offers an additional security to prevent damage. In addition, however, according to the invention leakage in the hose downstream from the hose roller pump may also be inferred. For example, if leakage occurs downstream from the hose roller pump, for example, due to material defects in the hose or in devices connected to it fluidically, such as dialysis filters, then the pressure and/or the fluid flow will deviate from the expected values. Likewise by monitoring the motor current of the hose roller pump, abnormal situations may be inferred; for example, the motor current may experience an unexpected increase if there is an occlusion at the pump outlet end.

In addition, other potentially dangerous situations can also be inferred. For example, if the connection of the hose to a dialysis filter downstream is completely disconnected from the hose roller pump, the fluid pressure drops suddenly and the flow velocity increases suddenly. The pump current in such a situation drops to unexpected values due to the sudden reduction in flow resistance.

In such a situation the control unit can stop the hose roller pump immediately and initiate further measures such as an alarm message to the attending medical personnel and disconnecting the patient from the extracorporeal blood circulation through appropriate actuators such as hose clamps.

Figure 4:
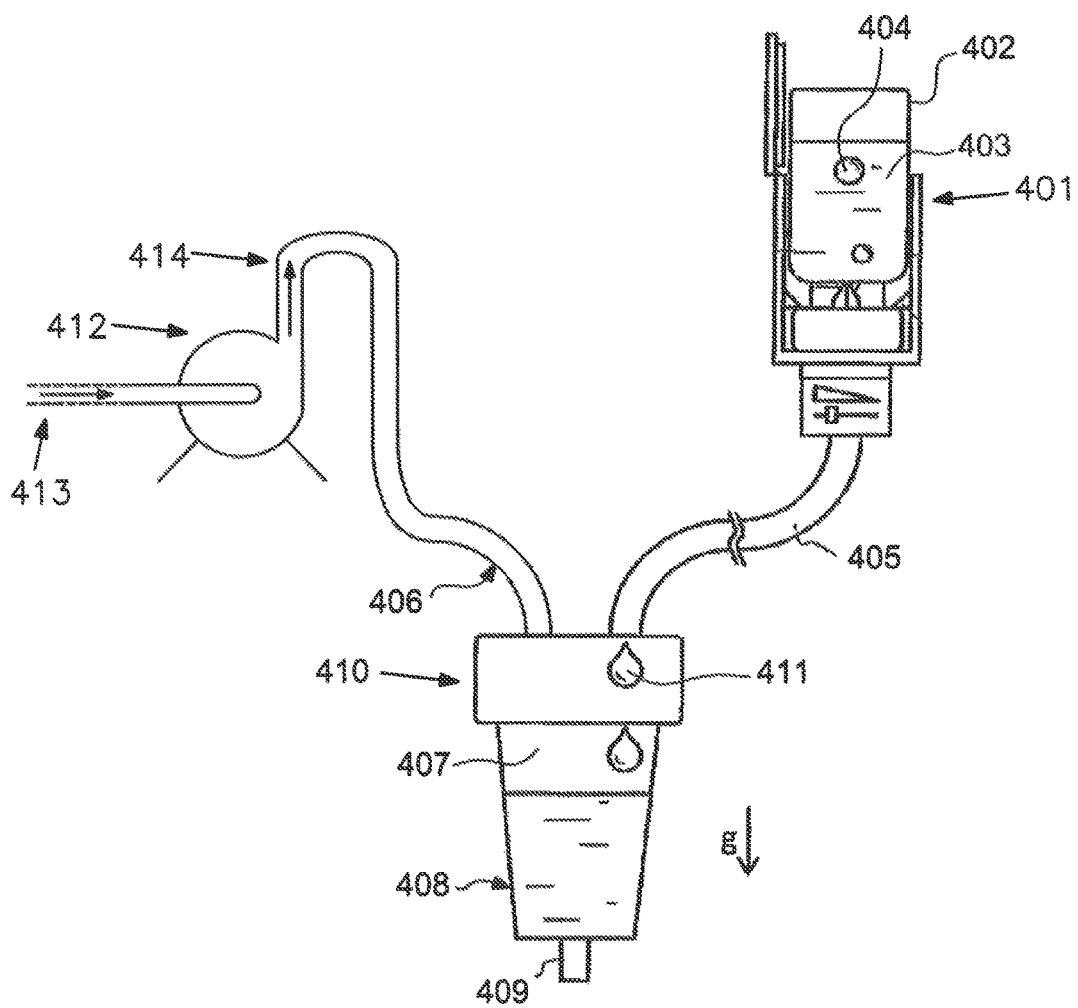
FIG. 4 shows a medication dosing device according to the invention in an exemplary embodiment.

FIG. 4 shows an example of an embodiment of a medication dosing device which is driven by a hose roller pump. This device is described in detail in unexamined European Patent EP 2 386 324 A1, to which reference is made explicitly here. FIG. 4 comprises a drip chamber 410 in which a fluid 408, for example, patient blood, is kept at a certain fluid level. Above this level there is air 407. The drip chamber 410 has an inlet 406 through which the fluid 408 enters the drip chamber, driven by a fluid pump. The fluid is removed from the drip chamber through the drain 409.

In addition, the drip chamber 410 has an additional hose connection 405 which connects the dosing device 401 to the drip chamber in a pressure-proof manner. A medication container 402 containing liquid medication 403 is kept in supply in the dosing device 401.

The pressure characteristic prevailing in the area 407 of the drip chamber is important for the dosing operation and acts on the dosing device 401 via the hose connection 405.

The dosing device is equipped with two non-return valves (not shown in detail here) whose through direction is rotated with respect to the other and which connect the hose connection 405 to the interior of the medication container 402. If the pressure in the drip chamber increases by a certain amount, for example, due to the pressure pulses of a hose roller pump delivering fluid into the drip chamber, then the non-return valve opens, leading from the hose line 405 into the medication container 402. Accordingly, an air bubble 404 is first forced out of the drip chamber and into the medication container 402. The pressure inside the medication container 402 then increases.

If the pressure in the drip chamber again drops by a certain amount, which is normal when using hose roller pumps for delivering fluid into the drip chamber, then the formerly open non-return valve closes again and the non-return valve which is rotated 180 degrees in relation to the former is opened. Accordingly, droplets 411 of the medication 403 are conveyed from the medication container 402 into the drip chamber and this is continued until the pressure difference between the medication container and the drip chamber is no longer sufficient to keep the non-return valve open.

Due to the periodic pressure fluctuations produced by a hose roller pump in the manner already described, the fluid is conveyed into the drip chamber via the hose line 406 when the hose roller pump is used as a fluid pump, periodically causing medication to be dispensed from the medication container 402.

This periodic dispensing of medication is often unwanted. However, causing the medication to be dispensed in a controlled manner is a desired goal. This is achieved by regulating the angular velocity of the rotor in the manner already described according to the invention when using hose roller pumps.

If, however, a centrifugal pump is used for conveying the fluid, then the problem of unwanted pressure fluctuations in the fluid conveyed does not arise because centrifugal pumps do not generate any pressure pulses at a constant rotational speed.

If a centrifugal pump with a medication dosing device like that shown in FIG. 4 is used, however, the problem is how to create pressure pulses in a controlled manner through appropriate control of the centrifugal pump to cause a controlled dispensing of medication.

This is accomplished according to the invention by varying the operating point of the centrifugal pump in accordance with a profile. It has been found that the centrifugal pumps conventionally used for medical purposes react with a change in the rotational speed and associated with this also with the change in the fluid pressure in response to the sudden change in the control signal within a sufficiently short period of time.

Figure 5:
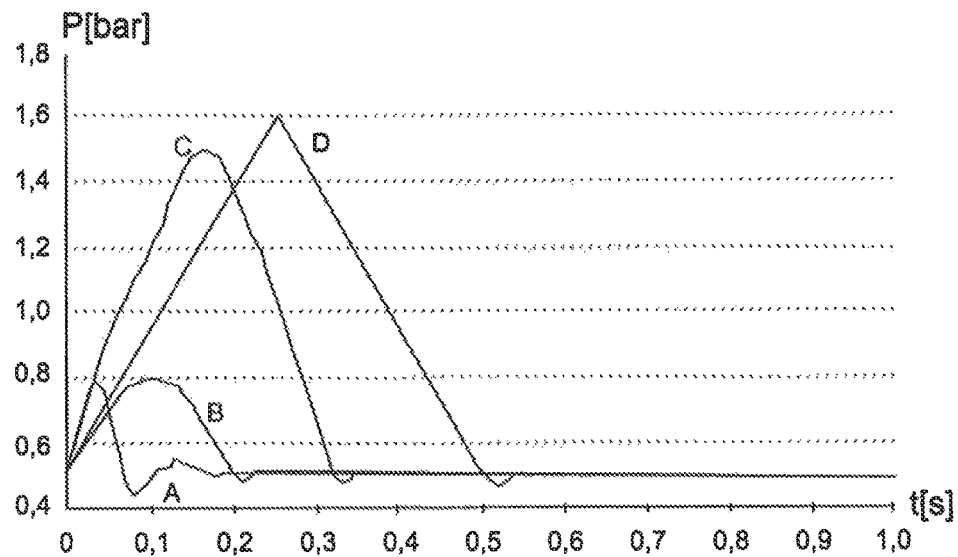
FIG. 5 shows the profiles of the output pressure and/or the rotational speed of the centrifugal pump of a device according to the invention.
Figure 5:
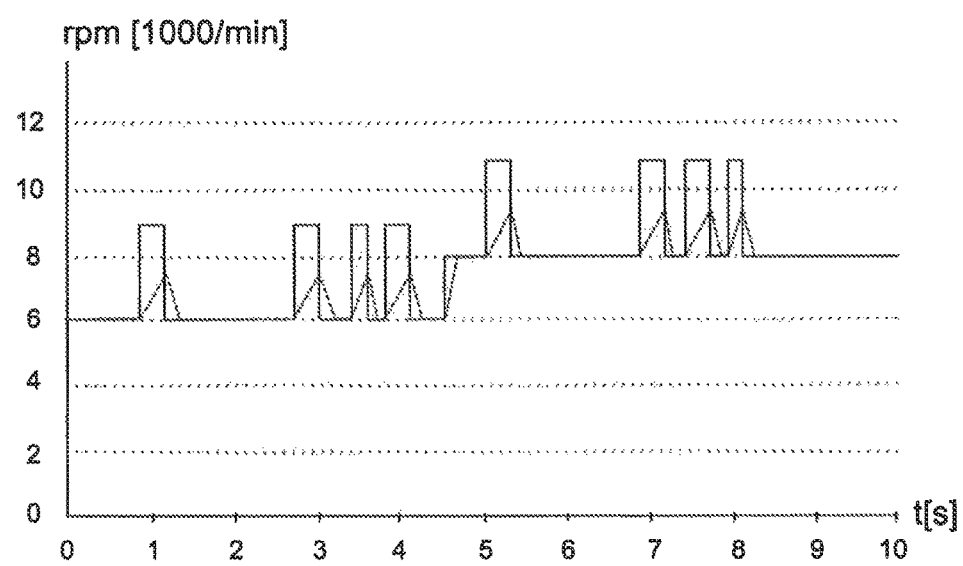

FIG. 5 shows two examples of this. The upper diagram in FIG. 5 shows the curve of the output pressure of a centrifugal pump, which is often used for medical purposes, when its rotational speed suddenly changes in a pulsating manner. The amount of the change is different for each of the curves labeled by letters A, B, C, D. It is essential that a change in the output pressure associated with that a change in the delivery rate within fractions of a second are passable.

The output pressure of a centrifugal pump can be varied on the basis of the profile according to the invention, as plotted in the bottom diagram in FIG. 5. The ordinate is plotted in revolutions per minute. This characteristic variable of a centrifugal pump is proportional to the output pressure and to the delivery rate, if the viscosity of the fluid delivered remains constant. The solid line in the bottom diagram in FIG. 5 indicates the control profile for the centrifugal pump and the interrupted dotted and dashed lines indicate the actual rotational speed of the centrifugal pump acted upon by this profile.

The pulsatile change in the output pressure may occur starting from any basic level as also shown by the lower diagram due to the two basic levels at 6000 revolutions per minute and at 8000 revolutions per minute.

In conjunction with a medication dosing device according to FIG. 4, control pressure pulses can be generated by this control in the drip chamber 410, leading to controlled dispensing of medication by the medication-dispensing device 401.

The regulating mechanisms described further above for the hose roller pump can also be used without restriction for the centrifugal pump. Here again, the input and output pressure as well as the current consumption by the centrifugal pump can be monitored and the results sent to a regulating circuit according to FIG. 3.

It is thus possible through the invention to simultaneously produce pumping operations that are gentle on the blood and to also generate controlled pressure pulses which in combination with a medication dosing device controlled in this way lead to controlled dispensing of medications.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A device for controlling a pump, said device comprising:
a centrifugal pump;
a medication dosing device; and
a control unit,
said medication dosing device being actuated by the centrifugal pump, and
said control unit controlling the centrifugal pump to create, in a controlled manner, pressure pulses which effect a controlled dispensing of the medication from the medication dosing device, with the control unit controlling the centrifugal pump by changing an operating point of the centrifugal pump according to a profile,
said profile including a first change from a first operating point to a second operating point, and a second change from the second operating point to the first operating point or to a third operating point,
the second operating point being associated with an operating parameter which is greater than or less than the operating parameter is when associated with the first operating point and the third operating point.

2. The device according to claim 1, wherein the control unit is configured to vary the operating point of the centrifugal pump during a calibration phase in accordance with a calibration profile, and to record at least one of the operating parameters and assign the recorded operating parameter to the respective operating point.

3. The device according to claim 1, wherein the control unit is configured to induce the dispensing of medication in a controlled manner by varying the operating point of the centrifugal pump.

4. The device according to claim 1, further comprising a sensor for detecting at least one of the operating parameters of the centrifugal pump, wherein the device is configured to transmit the detected operating parameter to the control unit.

5. A medical machine comprising:
a device for controlling a pump, said device including a centrifugal pump;
a medication dosing device; and
a control unit,
said medication dosing device being actuated by the centrifugal pump, and
said control unit controlling the centrifugal pump to create, in a controlled manner, pressure pulses which effect a controlled dispensing of the medication from the medication dosing device, with the control unit controlling the centrifugal pump by changing an operating point of the centrifugal pump according to a profile,
said profile including a first change from a first operating point to a second operating point, and a second change from the second operating point to the first operating point or to a third operating point,
the second operating point being associated with an operating parameter which is greater than or less than the operating parameter is when associated with the first operating point and the third operating point.

6. The medical machine according to claim 5, wherein the medical machine is a blood treatment machine.

7. A method of controlling a pump, said method comprising:
a step of changing an operating point of a centrifugal pump which actuates a medication dosing device, to create, in a controlled manner, pressure pulses which effect a controlled dispensing of the medication from the medication dosing device,
with the step of changing conforming to a profile which includes a first change from a first operating point to a second operating point, and a second change from the second operating point to the first operating point or to a third operating point,
the second operating point being associated with an operating parameter which is greater than or less than the operating parameter is when associated with the first operating point and the third operating point.

8. The method according to claim 7, wherein during a calibration phase, the operating point of the centrifugal pump is varied in accordance with a calibration profile, and at least one of the operating parameters is recorded and assigned to the respective operating point.

9. The method according to claim 7, wherein the dispensing of medication by the medication dosing device is effected in a controlled manner by the change in the operating point of the centrifugal pump.

10. The method according to claim 7, further comprising a step of detecting with a sensor at least one of the operating parameters of the centrifugal pump, wherein the detected operating parameter of the control unit is transmitted.

11. The method according to claim 7, wherein the change in the operating point of the centrifugal pump is effected in a system that includes at least two of the centrifugal pumps.

12. A method of controlling a medical machine having a control unit, said method comprising:
changing an operating point of a centrifugal pump which actuates a medication dosing device, to create, in a controlled manner, pressure pulses which effect a controlled dispensing of the medication from the medication dosing device,
with the change conforming to a profile which includes a first change from a first operating point to a second operating point, and a second change from the second operating point to the first operating point or to a third operating point,
the second operating point being associated with an operating parameter which is greater than or less than the operating parameter is when associated with the first operating point and the third operating point.

13. The method according to claim 12, wherein the medical machine is a blood treatment machine that performs hemodialysis, hemofiltration, hemodiafiltration, or plasmapheresis.

14. The medical machine according to claim 6, wherein the blood treatment machine is configured for hemodialysis, hemofiltration, hemodiafiltration, or plasmapheresis.

\* \* \* \* \*